United States Patent [19]

Kurpis

[11] Patent Number: 4,768,956
[45] Date of Patent: Sep. 6, 1988

[54] DENTAL IMPLANT

[76] Inventor: Albert J. Kurpis, 143 Brookside Ave., Rivervale, N.J. 07675

[21] Appl. No.: 913,211

[22] Filed: Sep. 29, 1986

Related U.S. Application Data

[63] Continuation of Ser. No. 651,622, Sep. 17, 1984, abandoned.

[51] Int. Cl.$^4$ .............................................. A61C 8/00
[52] U.S. Cl. ..................................... 433/173; 433/176
[58] Field of Search ................ 433/173, 174, 175, 176

[56] References Cited

U.S. PATENT DOCUMENTS

| | | | |
|---|---|---|---|
| 3,579,831 | 5/1971 | Stevens | 433/173 |
| 3,798,771 | 3/1974 | Edelman | 433/176 |
| 3,837,080 | 9/1974 | Pasqualini | 433/176 |
| 3,866,321 | 2/1975 | Valen | 433/176 |
| 3,952,414 | 4/1976 | Shovers | 433/173 |
| 3,977,081 | 8/1976 | Zambelli | 433/176 |
| 3,979,828 | 9/1976 | Taylor | 433/175 |
| 4,121,340 | 10/1978 | Patrick | 433/176 |
| 4,302,188 | 11/1981 | Driskell | 433/173 |
| 4,420,305 | 12/1983 | Linkow | 433/176 |
| 4,521,192 | 6/1985 | Linkow | 433/176 |

OTHER PUBLICATIONS

Park Dental Research Corp.-Implant Center Broshure.
Interplants, Inc., "F-S Implant Brochure.
Miter, Inc., (Titanaloy TM Anatomic Blade Series) Brochure.
Miter, Inc., (Titanodont Blades) Brochure.

Primary Examiner—John J. Wilson
Attorney, Agent, or Firm—Schechter, Brucker & Pavane

[57] ABSTRACT

A prosthetic dental implant (10) comprises a body (26) having a depression (12) in the upper portion thereof, en enlarged space (16) beneath the depression (12), at least one additional opening (14) therein, and a neck (18) joined to the body (26) substantially at the nadir (30) of the depression (12). A prosthetic dental implant (10) having entirely rounded surfaces beneath the gum line is also disclosed.

52 Claims, 2 Drawing Sheets

DENTAL IMPLANT

This is a continuation of U.S. Application Ser. No. 651,622, filed Sept. 17, 1984, now abandoned.

TECHNICAL FIELD

This invention pertains to oral prosthetic implants. The device is surgically implanted providing support means for one or more crown replacements and artificial teeth.

BACKGROUND ART

Teeth are lost due, among other things, to damage from accident or injury, or by disease. Replacing teeth which have been lost may be accomplished by using either a permanent or removeable bridge. In certain situations prosthetic restoration is desirable and dental implants are used. However, known dental prostheses have disadvantages which often result in failure of the implant. One cause of implant failure is infection. When an alloplastic material is introduced into bone tissue, resorption of the bone at the site of penetration occurs. The lost bone tissue is replaced by epithelium and connective tissue. This epithelial downgrowth, as it is known, provides a path for bacteria to penetrate the area around the implant beneath the gum line. Infection ensues, and can eventually lead to furca type involvement.

The configuration of known implants do not adequately address this problem. Moreover, once such infection does occur, their configurations are ill-suited for achieving adequate cleaning of the infected area, with the ultimate consequence of persistent infection and eventual implant failure.

The second major cause of implant failure results from chronic inflammation of the collagen capsule and associated bone tissue depletion. Dental implants are subjected to tremendous mechanical stress from biting and chewing. Known dental implants characteristically have corners and other sharp edges. It is these edges which damage the fragile collagen capsule which joins the implant to the surrounding bone tissue. This creates chronic inflammation surrounding the implant. The ultimate result is bone tissue dissolution and eventual implant failure.

It is therefore an object of the present invention to enhance success of dental prosthetic restoration by more effectively controlling bacterial infection.

It is a further object of the invention to extend the life of a dental prosthetic restoration by reducing trauma to the collagen capsule.

DISCLOSURE OF THE INVENTION

The implant in accordance with the present invention comprises a body having a depression in the upper surface thereof, an enlarged space beneath the depression, and at least one additional opening therein, and a neck joined to the body substantially at the nadir of the depression. The implant of the invention, and particularly the depression and the enlarged central space therebeneath, serve to retard bacterial infection of the tissue surrounding the implant, and to facilitate cleaning of such infection as does occur, all as will be more fully described below.

In a preferred embodiment, the body is substantially flat and of generally rectangular shape, and all the surfaces of the implant beneath the gum line are rounded to minimize trauma to the collagen capsule which forms about the implant following implantation. Also in the preferred embodiment, the neck is elongated, having an overall length of about 4–8 mm, thereby extending the time when epithelial downgrowth and accompanying bacterial infection ultimately reach the body of the implant.

The invention also comprises a dental implant comprising a body defining at least one opening therein, a neck secured to the body and extending upwardly therefrom, the body and at least the portion of the neck for disposition below the gum line being comprised of entirely rounded surfaces for minimizing trauma to the collagen capsule.

Further features and advantages of the dental implant in accordance with the present invention will be more fully apparent from the following detailed description and annexed drawings of the presently preferred embodiment thereof.

BRIEF DESCRIPTION OF THE DRAWINGS

In the drawings, wherein like numerals represent like parts.

BEST MODE FOR CARRYING OUT THE INVENTION

Figure 1:
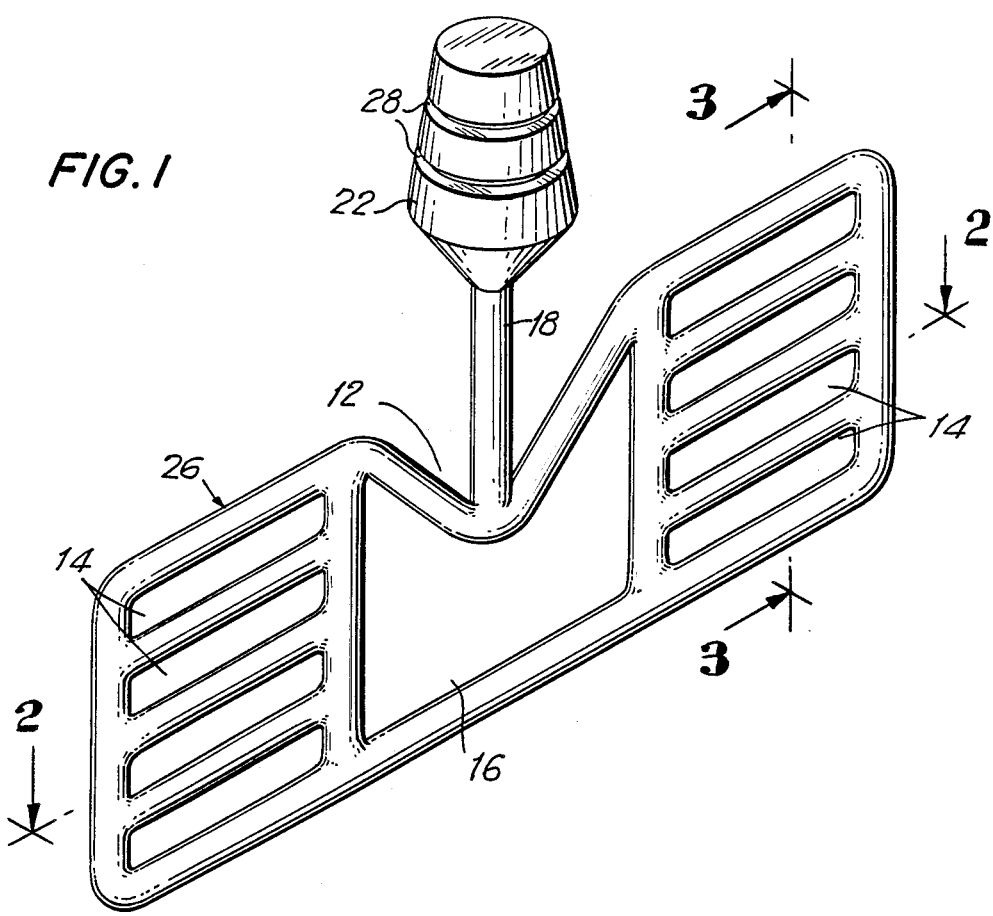
FIG. 1 is a perspective view of the dental implant in accordance with the present invention.

Referring now to the drawings, and initially to FIG. 1, 10 designates the preferred embodiment of the dental implant in accordance with the present invention.

Figure 3:
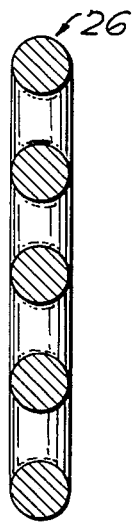
FIG. 3 is a cross-sectional view taken substantially along line 3—3 of FIG. 1 further illustrating the rounded surfaces of the dental implant of the invention.
Figure 2:
FIG. 2 is a cross-sectional view taken substantially along line 2—2 of FIG. 1 illustrating the rounded surfaces of the dental implant of the invention.

As shown in FIG. 1, the implant 10 has a substantially flat, rectangular body 26. A substantially V-shaped depression 12 is formed in the upper portion of the body 26 substantially at the midpoint thereof, and an enlarged space or opening 16 is provided in the body 26 beneath the depression 12. The portions of the body 26 on either side of the enlarged space 16 each define a plurality of elongated openings 14. A neck 18 of substantially uniform circular cross-section throughout is joined to the body 26 at the nadir of the depression 12. The neck has a height of about 4–8 mm and extends approximately 4 mm above the non-recessed upper surface of the body 26. A conventional frustum-shaped support post 22 is attached to the upper end of the neck 18. As best shown in FIGS. 1—3, all the surfaces of the body 26 and the neck 18 are rounded.

The preferred method of making the dental implant of the present invention includes preparing a mold from a plastic or wax pattern, then casting in a surgical grade alloy or other suitable material, such as plastic or ceramic. This conventional wax lost technique is within the knowledge of the person of ordinary skill in the art and a further description thereof is therefore deemed unnecessary. The body 26 of the preferred implant is approximately 18 gauge thickness, while the thickness of the neck is approximately 14 gauge.

In use, the dental prosthetic device 10 of the invention is surgically implanted in the jawbone such that the upper surface of the implant is generally between 2-3 mm below the bone level. With the prosthetic device 10 thus implanted, the frustum-shaped support post 22 protrudes above the gum line, and a crown or artificial tooth may be secured thereto as by a suitable adhesive. The support post 22 is provided with grooves 28 for receiving the adhesive for enhancing securement of the tooth or crown to the post 22.

Following implantation, bone tissue grows through the openings 14 and space 16 in the body 26 and serves to anchor the implant in place in the jawbone. It is desirable that the openings 14 on either side of the enlarged space 16 comprise smaller, elongate openings rather than larger openings. This is preferable because the structure of the body 26 defining these smaller openings 14 provides increased surface area for anchoring the implant 10 as the growth of surrounding bone tissue fills the openings 14. Also, by employing horizontal struts for defining horizontal openings 14, the vertical forces transmitted to the implant 10 during chewing, for example, are more evenly distributed and the life of the implant thereby prolonged. Consequently, by providing these smaller, elongate openings 14 on either side of the body 26 to provide sufficient anchoring, the opening 16 beneath the neck 18 may be enlarged for accomplishing the functions described below.

The preferred dental implant of the invention has several features which enhance its useful life by facilitating maintenance and slowing deterioration of surrounding tissue. One such feature is the central disposition of the neck 18 within the V-shaped depression 12. As noted previously, bone resorption and consequent epithelial downgrowth, which are normal reactions to insult with an alloplastic material, generally begins at the site where the implant penetrates the gum and bone i.e. at the neck of the implant. If the upper surface of the implant were not provided with the depression 12, epithelial downgrowth along the neck 18 would more rapidly reach the body 26. Once such furca-type involvement occurs, there is an enhanced probability of infection from bacteria which penetrates the tissue to the extent of the epithelial downgrowth. By recessing the neck-body junction 30 of the implant, epithelial downgrowth and hence bacterial infection of tissue surrounding the body 26 is delayed with consequent extension of the useful life of the implant. Moreover, cleaning of such bacterial invasion that does occur in the vicinity of neck 18 is facilitated by the configuration of the depression 12, which is wider at the top than at the bottom, as this configuration allows easy insertion of dental implements into the depression for combating bacterial infection.

Another feature of the invention which enhances its useful life is the provision of the large space 16 beneath the depression 12. More particularly, epithelial downgrowth typically follows the structural components of the implant. Therefore, a structural component extending directly from the bottom of the neck to the bottom of the body would provide a direct path for epithelial downgrowth and consequent deep infection. As will be apparent from FIG. 1, the large space 16 beneath the neck 18 in the implant 10 of the present invention avoids such a direct path thereby delaying if not reducing the occurrence of deep infection. Furthermore, upon occurrence of infection beneath the neck 18, the enlarged central space 16 facilitates cleaning and maintenance of the involved area as its size renders it more readily accessible to dental implements.

Also, the neck 18 of the preferred implant 10 is longer than those of prior art implants. In particular, in the preferred embodiment the neck extends approximately four millimeters above the top of the non-depressed regions of the upper surface of the body 26. This allows the device to be implanted somewhat deeper into the jawbone. In addition, there is an additional length of about 2-4 millimeters of neck extending into the depression 12. After the implant is surgically implanted, it is contemplated that about 4-8 millimeters of neck will be below the gum line, depending upon the implant site. Since the primary path of epithelial downgrowth is along the neck, it will be appreciated that this longer length of neck 18 between the gum line and the body 26 will delay epithelial downgrowth and resulting bacterial infection from reaching the body 26. This is advantageous since, as noted above, bacterial infection is more difficult to treat once it reaches the body 26.

Another feature of the preferred dental implant of the invention is the provision of all rounded surfaces which serves to reduce damage to the collagen capsule which forms around the implant following implantation. More specifically, the junction between the dental implant and the collagen capsule is subjected to repeated and severe mechanical stress from chewing and biting. Such mechanical stresses are highest at sharp edges or corners of known implants, and rupture of the collagen capsule typically occurs at these sites. The result is chronic inflammation and dissolution of surrounding bone tissue which often leads to implant failure. Here, on the other hand, the rounded surfaces of the preferred dental implant according to the invention reduce the incidence of trauma to the collagen capsule, thereby reducing bone dissolution and increasing the implant's useful life.

Figure 4:
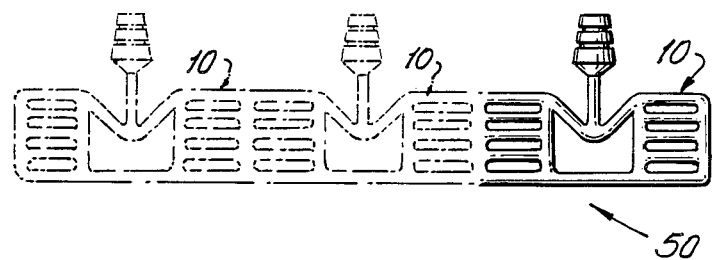
FIG. 4 is an elevational view of an embodiment of the invention for supporting multiple teeth or crowns.

Referring now to FIG. 4, a multiplicity of implants 10 of the type illustrated in FIGS. 1-3 are integrally joined, side-by-side, to form a single implant 50 capable of supporting a plurality of artificial teeth or crowns. Except for the fact that they are integrally joined, each unit of the implant 50 is identical to the implant 10 described above and hence incorporates all of the features and advantages thereof.

Figure 5:
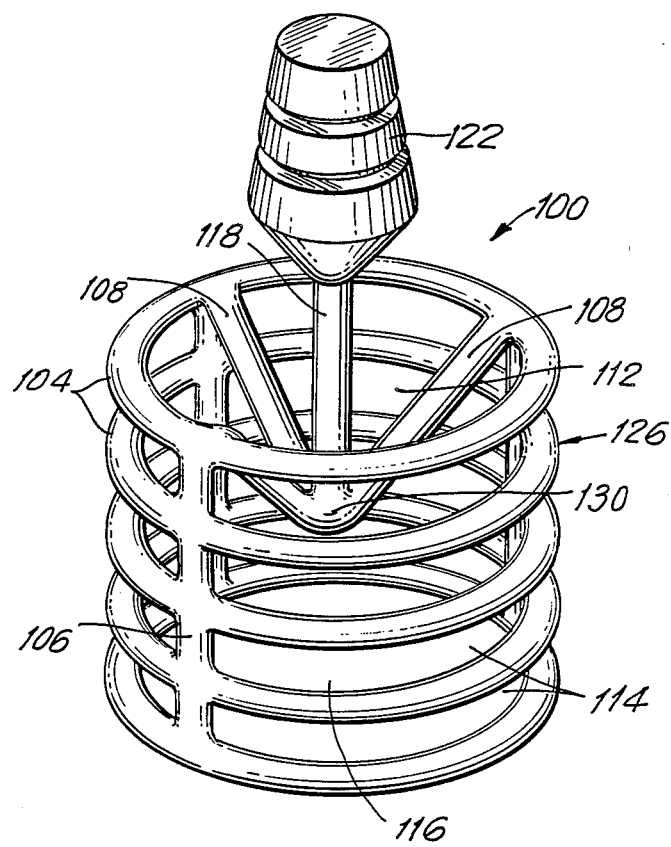
FIG. 5 is a perspective view of an alternative embodiment of a dental implant according to the invention.

Referring now to FIG. 5, an alternative embodiment of an implant in accordance with the present invention is generally designated at 100. The implant 100 embodies the operative structural features of the implant 10 of FIGS. 1-3, the primary difference being that the body 126 of the implant 100 is of open cylindrical construction as contrasted with the flat rectangular construction of the implant 10. The implant 100 may be used for example in an extract site or a wide buccal lingual bone dimension.

As shown, the body 126 of the implant 100 comprises a plurality of equidistant, horizontally oriented annular tiers 104, shown by way of example as five annular tiers, joined by a plurality of vertical support rods 106, shown by way of example as three equidistant support rods. The annular elements 104 and vertical rods 106 define a multiplicity of horizontally extending openings 114 which serve the same function as the openings 14 of the embodiment of FIGS. 1-3.

A central depression 112 is formed in the top of the implant 100 by a plurality of angled struts 108, each of which is joined at one end to the upper annular element 104 and at the other end to each other at a point of intersection 130 beneath the top of the body 126. The struts 108 are joined at the point of intersection 130 with the neck 118 which has the usual support post 122 at its upper end. It will therefore be appreciated that the struts 108 define a central depression 112 about the neck 118 which serves the same function as the depression 12 in the implant 10 of the embodiment of FIGS. 1-3. It will also be appreciated that an enlarged space 116 is defined in the body 126 beneath the central depression 112. Again, this enlarged space 116 serves the same function as the enlarged space 16 beneath the depression 12 in the embodiment of FIGS. 1-3. Finally, and as is also true of the embodiment of FIGS. 1-3, all of the surfaces of the implant 100 of FIG. 5 are rounded for reducing the incidence of trauma to the collagen capsule.

While I have herein shown and described the preferred embodiment of the present invention, persons of ordinary skill in the art will recognize that changes and modifications may be made therein without departing from the spirit and scope of the invention. For example, while the recessed area 12 in the upper surface of the body 26 is shown and described as substantially V-shaped, it will be appreciated that the depression 12 may have other suitable shapes, such as semicircular. The number and shape of the openings 14 on either side of the enlarged opening 16 may likewise be varied. Also, specially designed necks 18 may be employed for special applications. For example, the length of the neck 18 may be varied from the dimensions given above. Likewise, the orientation or the neck with respect to the body 26 may be other than vertical.

As a further alternative especially suited for implants following extraction or in other situations requiring healing without disturbance, the support 22 may be formed separately from the neck 18. In this embodiment, the neck 18 is provided with internal threads for receiving external threads at the bottom of the support post 22. In use of this embodiment, the body 26 and connected neck 18 is first surgically implanted in the jawbone with the height of the neck being selected such that the top thereof is beneath the gum line. After healing, a second incision is made to expose the top of the neck whereupon the support post 22 may be threaded thereon. Then, a crown or artificial tooth may be secured to the post 22. As noted, this embodiment is particularly useful for procedures following tooth extraction, as it permits embedding the device into a recent extraction site while allowing time for healing before effecting tooth replacement. In the absence of the support post 22 and the artificial tooth or crown, there is little mechanical stress transmitted to the implanted body 26, and hence healing is facilitated.

Still further changes and modifications will suggest themselves to those skilled in the art once this description is known. Accordingly, the above description should be construed as illustrative, and not in a limiting sense, the scope of the invention being defined by the following claims.

I claim:
1. A prosthetic dental implant comprising
a substantially flat body having a top wall, said top wall including a depressed section defining a depression in the upper portion of the body, said body having an enlarged space beneath the depression with the top of said enlarged space being defined, at least in part, by said depresed section of said top wall; and at least one additional opening in said body, said body being disposed wholly within bone when said implant is in place; and
a neck joined to the body substantially at the nadir of the depression, said neck comprising the sole portion of the implant extending through the bone when the implant is in place.

2. The prosthetic dental implant according to claim 1, wherein all of the surfaces of said body, and at least the surface of the portion of the neck which will be disposed beneath the gum line, are comprised of entirely rounded surfaces.

3. The prosthetic dental implant according to claim 2, wherein said body and said neck are comprised of members having circular cross sections.

4. The prosthetic dental implant according to claim 2, wherein said depression is wider at the top than at the bottom.

5. The prosthetic dental implant according to claim 4, wherein said enlarged space occupies substantially the full height of said body beneath said depression.

6. The prosthetic dental implant according to claim 5, wherein a plurality of additional openings are provided in said body.

7. The prosthetic dental implant according to claim 6, wherein said space is centrally located, and a plurality of openings are provided on either side of said space.

8. The prosthetic dental implant according to claim 7, wherein said body is of generally rectangular shape.

9. The prosthetic dental implant according to claim 7, wherein said neck extends about 2-4 mm above the non-depressed region of the upper portion of said body, and wherein the overall height of said neck is about 4-8 mm.

10. The prosthetic dental implant according to claim 1, wherein said depression is wider at the top than at the bottom.

11. The prosthetic dental implant according to claim 10, wherein said depression is substantially V-shaped.

12. The prosthetic dental implant according to claim 10, wherein the nadir of said depression is substantially at the center thereof.

13. The prosthetic dental implant according to claim 1, wherein said enlarged space occupies substantially the full height of said body beneath said depression.

14. The prosthetic dental implant according to claim 13, wherein the width of said central space is substantially the same as the width of the widest portion of said depression.

15. The prosthetic dental implant according to claim 1, wherein a plurality of additional openings are provided in said body.

16. The prosthetic dental implant according to claim 15, wherein said additional openings are elongate and horizontally oriented.

17. The prosthetic dental implant according to claim 1, wherein said space is centrally located in said body, and a plurality of openings are provided on either side of said space.

18. The prosthetic dental implant according to claim 17, wherein said body is of generally rectangular shape.

19. The prosthetic dental implant according to claim 1, wherein said neck extends about 2-4 mm above the non-depressed region of the upper portion of said body, and wherein the overally height of said neck is about 4-8 mm.

20. The prosthetic dental implant according to claim 1, wherein the implant is cast in surgical grade alloy.

21. The prosthetic dental implant according to claim 1, and further comprising a support post for receiving an artificial tooth or crown secured to the upper end of said neck.

22. The prosthetic dental implant according to claim 21, wherein said support post is integrally joined to said neck.

23. The prosthetic dental implant according to claim 21, wherein said support post is releasably secured to said neck, and further comprising means for releasably securing said support post to said neck.

24. The prosthetic dental implant comprising a three-dimensional body, said body having a depression in the upper portion thereof defined by a plurality of members having voids therebetween, said body having an enlarged space beneath said depression accessible for cleaning through said voids, said body having at least one additional opening therein and being disposed wholly within the bone when said implant is in place; and a neck joined to said body substantially at the nadir of said depression, said neck comprising the sole portion of the implant extending through the bone when the implant is in place.

25. The prosthetic dental implant according to claim 24, wherein said body is substantially cylindrical.

26. The prosthetic dental implant according to claim 25, wherein said body comprises a plurality of horizontal annular elements and a plurality of vertical supports connecting said annular elements, and wherein said at least one additional opening comprises a plurality of elongate horizontal openings between said annular elements and said vertical supports.

27. The prosthetic dental implant according to claim 24, wherein all of the surfaced of said body, and at least the surface of the portion of the neck which will be disposed beneath the gum line, are comprised of entirely rounded surfaces.

28. The prosthetic dental implant according to claim 27, wherein said body and said neck are comprised of members having circular cross sections.

29. The prosthetic dental implant according to claim 24, wherein said depression is wider at the top than at the bottom.

30. The prosthetic dental implant according to claim 29, wherein said depression is substantially cone-shaped.

31. The prosthetic dental implant according to claim 29, wherein the nadir of said depression is substantially at the center thereof.

32. The prosthetic dental implant according to claim 24, wherein said enlarged space occupies substantially the full height of said body beneath said depression.

33. The prosthetic dental implant according to claim 32, wherein the width of said central space is substantially the same as the width of the widest portion of said depression.

34. The prosthetic dental implant according to claim 24, wherein a plurality of additional openings are provided in said body.

35. The prosthetic dental implant according to claim 34, wherein said additional openings are elongate and horizontally oriented.

36. The prosthetic dental implant according to claim 34, wherein said body comprises a plurality of horizontal annular elements and a plurality of vertical supports connecting said annular element, and wherein said plurality of additional openings are defined by a plurality of elongate horizontal openings between said annular elements and said vertical supports.

37. The prosthetic dental implant according to claim 24, wherein said neck extends about 2–4 mm above the non-depressed region of the upper portion of said body, and wherein the overall height of said neck is about 4–8 mm.

38. The prosthetic dental implant according to claim 24, and further comprising a support post for receiving an artificial tooth or crown secured to the upper end of said neck.

39. The prosthetic dental implant according to claim 38, wherein said support post is releasably secured to said neck, and further comprising means for releasably securing said support post to said neck.

40. A prosthetic dental implant comprising a substantially flat body with at least one opening therein, said body having a depression in the upper portion thereof, the body being disposed wholly within the bone when said implant is in place; and a neck joined to the body substantially at the nadir of the depression which is no deeper than one-half the overall height of the body, said neck having a height in the range of 4–8 mm with about 2–4 mm extending above the non-recessed region of the upper portion of said body, the neck comprising the sole portion of the implant extending through the bone when the implant is in place.

41. The prosthetic dental implant of claim 40, and further comprising an enlarged space beneath said depression accessible for cleaning from either side of said body.

42. The prosthetic dental implant according to claim 41, wherein the width of said enlarged space is substantially the same as the width of the widest portion of said depression.

43. The prosthetic dental implant according to claim 42, wherein a plurality of additional openings are provided in said body.

44. The prosthetic dental implant according to claim 43, wherein said additional openings are elongate and horizontally oriented.

45. The prosthetic dental implant according to claim 40, wherein all of the surfaces of said body, and at least the surface of the portion of the neck which will be disposed beneath the gum line, are comprised of entirely rounded surfaces.

46. The prosthetic dental implant according to claim 45, wherein said body and said neck are comprised of members having circular cross sections.

47. The prosthetic dental implant according to claim 40, wherein said depression is wider at the top than at the bottom.

48. The prosthetic dental implant according to claim 47, wherein said depression is substantially V-shaped.

49. The prosthetic dental implant according to claim 40, wherein the nadir or said depression is substantially at the center thereof.

50. The prosthetic dental implant according to claim 40, and further comprising a support post for receiving an artificial tooth or crown secured to the upper end of said neck.

51. The prosthetic implant comprising a three-dimensional body, said body having a drpression in the upper portion thereof defined by a plurality of members having voids therebetween, said body having at least one opening therein and being disposed wholly within the bone when said implant is in place; and a neck joined to the body at substantially the nadir of the depression which is no deeper than one-half the overall height of the body, said neck having a height in the range of 4–8 mm with about 2–4 mm extending above the non-depressed region of the upper portion of said body, the neck comprising the sole portion of the implant extending through the bone when the implant is in place.

52. The prosthetic dental implant of claim 51, and further comprising an enlarged space beneath said depression accessible for cleaning from either side of said body.

* * * * *